(12) United States Patent
Takenaka et al.

(10) Patent No.: US 9,480,672 B2
(45) Date of Patent: Nov. 1, 2016

(54) INTERNAL COMPOSITION

(71) Applicant: LION CORPORATION, Sumida-ku (JP)

(72) Inventors: Hiroki Takenaka, Tokyo (JP); Yasuharu Ishihara, Tokyo (JP); Naoki Ichiyanagi, Tokyo (JP); Misato Koakutsu, Tokyo (JP); Kei Kurita, Tokyo (JP)

(73) Assignee: LION CORPORATION, Sumida-ku (JP)

( * ) Notice: Subject to any disclaimer, the term of this patent is extended or adjusted under 35 U.S.C. 154(b) by 0 days.

(21) Appl. No.: 14/787,399

(22) PCT Filed: Jul. 10, 2014

(86) PCT No.: PCT/JP2014/068485
§ 371 (c)(1),
(2) Date: Oct. 27, 2015

(87) PCT Pub. No.: WO2015/005443
PCT Pub. Date: Jan. 15, 2015

(65) Prior Publication Data
US 2016/0067203 A1 Mar. 10, 2016

(30) Foreign Application Priority Data
Jul. 10, 2013 (JP) .................................. 2013-144388

(51) Int. Cl.
| | |
|---|---|
| *A61K 31/202* | (2006.01) |
| *A61K 31/07* | (2006.01) |
| *A61K 31/122* | (2006.01) |
| *A61K 31/047* | (2006.01) |
| *A61K 31/12* | (2006.01) |
| *A23L 1/30* | (2006.01) |

(52) U.S. Cl.
CPC ............ *A61K 31/202* (2013.01); *A23L 1/3002* (2013.01); *A23L 1/3006* (2013.01); *A23L 1/3008* (2013.01); *A61K 31/047* (2013.01); *A61K 31/07* (2013.01); *A61K 31/12* (2013.01); *A61K 31/122* (2013.01); *A23V 2002/00* (2013.01)

(58) Field of Classification Search
CPC . A61K 31/202; A61K 31/122; A61K 31/107
USPC ........................................................ 514/560
See application file for complete search history.

(56) References Cited

U.S. PATENT DOCUMENTS

2007/0032548 A1 2/2007 Ellis
2010/0209523 A1 8/2010 Ueda

FOREIGN PATENT DOCUMENTS

| CN | 101262863 A | 9/2008 |
|---|---|---|
| CN | 101854815 A | 10/2010 |
| JP | 7-143862 A | 6/1995 |
| JP | 10-59844 A | 3/1998 |
| JP | 2008-179632 A | 8/2008 |
| JP | 2013-53109 A | 3/2013 |
| WO | 2006/116755 A2 | 11/2006 |

OTHER PUBLICATIONS

Suganuma, H., et al., "Amelioratory Effect of Dietary Ingestion with Red Bell Pepper on Learning Impairment in Senescense-Accelerated Mice (SAMP8)", Journal of Nutritional Science and Vitaminology, vol. 45, No. 1, 1999, pp. 143-149.
Johnson, E.J., "A possible role for lutein and zeaxanthin in cognitive function in the elderly", The American Journal of Clinical Nutrition, vol. 96, No. 5, 2012, 5 pages.
Hossain, S., et al., "Mechanism of docosahexaenoic acid-induced inhibition of in vitro $A\beta_{1-42}$ fibrillation and $A\beta_{1-42}$ —induced toxicity in SH-S5Y5 cells", Journal of Neurochemistry, vol. 111, No. 2, 2009, pp. 568-579.
Grimm, M.O.W., et al., "Docosahexaenoic Acid Reduces Amyloid β Production via Multiple Pleiotropic Mechanisms", The Journal of Biological Chemistry, vol. 286, No. 16, 2011, pp. 14028-14039.
Katayama, S., et al., "Apricot Carotenoids Possess Potent Antiamyloidogenic Activity in Vitro", Journal of Agricultural and Food Chemistry, vol. 59, No. 23, 2011, pp. 12691-12696.
Suganami, H., et al., "Amelioration of Learning Impairment by Docosahexaenoic Acid in SAMP8 Mice" (with partial English translation), The Journal of the Osaka Odontological Society, vol. 58, No. 6, Dec. 1995, pp. 435-446.
Sakayori, N., et al., "Distinctive effects of arachidonic acid and docosahexaenoic acid on neural stem/progenitor cells", Genes to Cells, vol. 16, Issue 7, 2011, pp. 778-790.
International Search Report Issued Oct. 7, 2014 in PCT/JP14/068485 Filed Jul. 10, 2014.
Office Action in CN application No. 201480025123.9 mailed Sep. 23, 2016.

*Primary Examiner* — Kristin Vajda
(74) *Attorney, Agent, or Firm* — Oblon, McClelland, Maier & Neustadt, L.L.P.

(57) ABSTRACT

An object of the present invention is to provide an internal composition capable of exerting various physiological functions such as a brain-function improving function. That is, the present invention provides an internal composition including docosahexaenoic acid and capsanthin, or docosahexaenoic acid, capsanthin, lutein, and zeaxanthin as active ingredients.

4 Claims, No Drawings

INTERNAL COMPOSITION

TECHNICAL FIELD

The present invention relates to an internal composition.

BACKGROUND

Symptoms caused by deterioration in brain functions include dementia such as an Alzheimer's disease. The number of Alzheimer's disease patients is approximately 2 million at present and is estimated to increase to 4 million until 2045. This is a very serious social problem to Japan facing an aging society. Although there are some therapeutic agents for the Alzheimer's disease, no fundamental therapeutic method thereof has been established up to date.

Although the causes of the Alzheimer's disease haven't been solved yet, an amyloid β-protein is closely related to the onset of the Alzheimer's disease. Thus it is believed that inhibition of synthesis and accumulation of the amyloid β (Aβ) is crucial in pursuit of achieving a complete cure. For this goal, therapeutic agents have been under development using various strategies that involve β and γ-secretase inhibitors, neutralizing antibodies against Aβ, activation of neprilysin functioning as an Aβ degrating enzyme, and the like, however satisfactory therapeutic agents have not been obtained yet.

The reason for this is that accumulation of Aβ in the brain has reached an advanced stage and brain neurons have died by the time the Alzheimer's disease is diagnosed, making it harder to treat the disease in this circumstance. Consequently, there is a need to develop a therapeutic agent and a method prophylactically functioning in the prevention of nerve cell death by prophylactically removing Aβ before the disappearance of nerve cells, or a therapeutic agent and a method for maintaining and restoring the number of nerve cells by proliferating and differentiating neural stem cells in the brain even if nerve cells are caused to die.

Patent Literature 1 describes that an antioxidant including any two or more kinds of carotenoids, ascorbic acids, and tocopherols exhibits anti-oxidation ability in vitro. It is considered that oxidation stress is involved in the disturbance of nerve cells.

Further, as an effect of docosahexaenoic acid (DHA), there are many reports describing that it is effective in preventing deterioration of brain functions in addition to lowering blood lipids, exerting antithrombotic activity, and the like. It is also reported that a combination of DHA and lutein has an inhibitory effect on deterioration of brain functions (Patent Literature 2). However, according to meta-analyses of intervention studies on DHA, the effectiveness of DHA is yet to be proved.

Non-Patent Literature 1 shows that DHA, arachidonic acid, and the like have a proliferation effect of neural stem cells.

RELATED ART DOCUMENTS

Non Patent Literature

Non Patent Literature 1: Genes to Cells, Volume 16, Issue 7, pages 778-790, July 2011

Patent Literature

Patent Literature 1: Japanese Patent Application Laid-Open No. 2008-179632
Patent Literature 2: International Publication No. 2006/116755

SUMMARY OF THE INVENTION

Problem to be Solved by the Invention

The anti-oxidation ability in Patent Literature 1 is observed in vitro, and it is not known if the anti-oxidation ability observed in vitro has any relevance to brain functions or accumulation of amyloid β in the brain. By such reason, it seems impossible to determine that the antioxidant described in Patent Literature 1 is an effective brain function-improving agent in vivo. Further, in Non Patent Literature 1, effectiveness on brain functions in a living body has yet to be determined.

An object of the present invention is to provide an internal agent or an internal composition, capable of exerting a brain function-improving function and/or an inhibitory function on amyloid β accumulation in the brain.

Means for Solving Problem

The present invention provides the following [1] to [6].
[1] An internal agent including one or more kinds selected from the group consisting of docosahexaenoic acid, capsanthin, capsorbin, fucoxanthin, and fucoxanthinol as active ingredients.
[2] The internal agent according to the above-described [1], including at least docosahexaenoic acid and capsanthin as active ingredients.
[3] The internal agent according to the above-described [1] or [2], being a brain function-improving agent.
[4] The internal agent according to the above-described [1] or [2], being an inhibitor of amyloid β accumulation in the brain.
[5] The internal agent according to the above-described [1], being a neural stem cell activator.
[6] The internal agent according to the above-described [1] or [2], being a RAGE gene expression inhibitor.

The present invention provides following [7] to [10], specifically.
[7] An internal composition comprising: docosahexaenoic acid and capsanthin; or docosahexaenoic acid, capsanthin, lutein, and zeaxanthin.
[8] The internal composition according to [7], wherein the internal composition is a brain-function improving composition.
[9] The internal composition according to [7], wherein the internal composition is a composition for inhibiting amyloid β accumulation in the brain.
[10] The internal composition according to any of [7] to [9], wherein an active ingredient is docosahexaenoic acid, capsanthin, lutein, and zeaxanthin.

Effect of the Invention

According to the present invention, an internal composition capable of exerting a brain function-improving function and an inhibitory function on amyloid β accumulation in the brain is provided.

Embodiments for Carrying out the Invention

The agent or the composition of the present invention may include docosahexaenoic acid (DHA) and/or a carotenoid. Examples of the carotenoid may include capsanthin, capsorbin, fucoxanthin, fucoxanthinol, zeaxanthin, and lutein. These may be used alone, or alternatively two or more of them may be used in combination. It is noted that, in this specification, a product is referred to as an agent if a single ingredient is used, while a product is referred to as a composition if two or more ingredients are used.

Docosahexaenoic acid (DHA, (4Z,7Z,10Z,13Z,16Z,19Z)-docosa-4,7,10,13,16,19-hexaenoic acid) may be derived from natural products that include animals such as fishes and microorganisms (*Schizochytrium* sp.), artificially produced, produced by gene recombination, or obtained from commercial products. Further, two or more kinds of DHA obtained by a variety of acquisition methods may be used in combination. DHA may be in a form of a pharmacologically acceptable salt.

DHA may be in a form of a free fatty acid or a derivative of DHA. Examples of the DHA derivative may include a DHA in triglyceride form (TG-DHA) and a DHA in phospholipid form. A DHA in triglyceride form is a chemical compound in which triglycerol and DHA are ester-bonded. In a DHA in triglyceride form, one or more molecules of DHA, in a form of a fatty acid, can be bound per molecule of triglycerol. Among DHAs in triglyceride form, a preferable DHA in triglyceride form is the one in which two or more molecules of DHA are bound per molecule of triglycerol. A DHA in phospholipid form is a chemical compound in which DHA is bound to a phospholipid such as phosphatidylcholine and phosphatidylserine. DHA in phosphatidylcholine form (PC-DHA) is preferable as a DHA in phospholipid form. Among DHAs in phospholipid form, a preferable DHA in phospholipid form is the one in which two or more molecules of DHA are bound per molecule of phospholipid. It is known that a DHA in phospholipid form is high in bioabsorbability, transitional activity to the brain, and oxidation stability as compared with a DHA in triglyceride form, thus a DHA in phospholipid form is more preferable among DHAs.

Capsanthin (all-trans-capsanthin, (3R,3'S,5'R)-3,3'-dihydroxy-β,κ-carotene-6'-one, and (3R,3'S)-3,3'-dihydroxy-β,κ-carotene-6'-one) may be derived from natural products that include plants such as paprika and capsicum, artificially produced, produced by gene recombination, or obtained from commercial products. Capsanthin may be in a form of a pharmacologically acceptable salt.

Capsorbin ((2S,2'S,5R,5'R)-2,2'-dihydroxy-κ,κ-carotene-6,6'-dione and (3S,3'S,5R,5'R)-3,3'-dihydroxy-κ,κ-carotene-6,6'-dione) may be derived from natural products that include plants such as paprika and capsicum, artificially produced, produced by gene recombination, or obtained from commercial products. Capsorbin may be in a form of a pharmacologically acceptable salt.

Fucoxanthin (Acetic acid [(1S,3R)-3-hydroxy-4-[(3E,5E,7E,9E,11E,13E,15E)-18-[(1S,4S,6R)-4-hydroxy-2,2,6-trimethyl-7-oxabicyclo [4.1.0]heptane-1-yl]-3,7,12,16-tetramethyl-17-oxooctadeca-1,3,5,7,9,11,13,15-octaenylidene]-3,5,5-trimethylcyclohexyl] ester) may be derived from natural products that include brown algae such as Kombu (kelp), Hijiki, and Wakame, artificially produced, produced by gene recombination, or obtained from commercial products. Fucoxanthin may be in a form of a pharmacologically acceptable salt.

Fucoxanthinol ((3S,3'S,5R,5'R,6S,6'S)-6',7'-didehydro-5,6-epoxy-5,5',6,6',7,8-hexahydro-3,3',5'-trihydroxy-8-oxo-β,β-carotene) may be derived from natural products that include brown algae such as Kombu, Hijiki, and Wakame, artificially produced, produced by gene recombination, or obtained from commercial products. Fucoxanthinol may be in a form of a pharmacologically acceptable salt.

Zeaxanthin (4-[18-(4-hydroxy-2,6,6-trimethyl-1-cyclohexenyl)-3,7,12,16-tetramethyl-octadeca-1,3,5,7,9,11,13,15,17-nonaenyl]-3,5,5-trimethyl-3-cyclohexene-1-ol) is represented by the following formula. Zeaxanthin may be derived from natural products that include plants (corn, etc.), egg yolks, and animal fats, artificially produced, produced by gene recombination, or obtained from commercial products. Zeaxanthin may be in a form of a pharmacologically acceptable salt.

Lutein (β,ε-carotene-3,3'-diol) may be derived from natural products that include chloroplasts in higher plants (spinach, kale, Komatsuna (Japanese mustard spinach), etc.), artificially produced, produced by gene recombination, or obtained from commercial products. Lutein may be in a form of a pharmacologically acceptable salt.

Examples of the pharmacologically acceptable salts in the present invention may include inorganic acid salts such as hydrochlorides, hydrobromides, sulfates, hydroiodides, nitrates, and phosphates, organic acid salts such as citrates, oxalates, acetates, formates, propionates, benzoates, trifluoroacetates, maleates, tartrates, methanesulfonates, benzenesulphonates, or para-toluenesulfonates; inorganic base salts such as sodium salts, potassium salts, calcium salts, magnesium salts, and ammonium salts; organic base salts such as triethylammonium salts, triethanolammonium salts, pyridinium salts, and diisopropylammonium salts; and amino acid salts such as arginine, aspartic acid, and glutamic acid.

Among the above ingredients, one kind thereof may be selected as an active ingredient to prepare an internal agent including the active ingredient, or two or more kinds thereof may be selected in combination as an active ingredient to prepare an internal composition including the active ingredients. Of those, an internal composition including DHA and capsanthin, or DHA, capsanthin, lutein, and zeaxanthin can exert a brain function-improving function and an inhibitory function on amyloid β accumulation in the hippocampus, and is thus preferable.

Among the above ingredients, a combination of DHA and capsanthin exerts a brain function-improving effect, and can be therefore used as active ingredients for a brain function-improving composition. As the active ingredients for a brain function-improving composition, DHA and capsanthin, or DHA, lutein, zeaxanthin, and capsanthin are preferable and a combination of DHA, lutein, zeaxanthin, and capsanthin is more preferable. According to this, a remarkable brain function-improving effect can be exerted.

A brain function may also be expressed as a cognitive function. A brain function usually refers to a higher brain function, which comprehensively covers a series of functions achieved by information processing in the brain, such as judgment, calculation, memory, understanding, learning, thought, and language. Improving a brain function means that a brain function described above, i.e., a cognitive function is improved.

Among the above ingredients, DHA and capsanthin can exert an effect of inhibiting amyloid β accumulation in the brain, especially in the hippocampus, and can thus be used as active ingredients for an inhibitory agent of amyloid β accumulation in the brain. As the active ingredients for an inhibitory agent of amyloid β accumulation in the brain, DHA and capsanthin, or DHA, lutein, zeaxanthin, and capsanthin are preferable, and a combination of DHA, lutein, zeaxanthin, and capsanthin is more preferable. According to this, a remarkable effect of inhibiting amyloid β accumulation in the brain can be exerted.

There are no particular limitations on dosages of the agent and the composition of the present invention so long as the effects of the present invention are not impaired, and the dosages may be appropriately adjusted according to various factors such as the age and conditions of a living body to be administered. Preferred dosages for obtaining the intended effects may be appropriately determined according to an intended purpose of the agent and the composition.

A daily dose of DHA is preferably 50 mg to 3,000 mg and preferably 100 mg to 2,200 mg. A daily dose of carotenoids is preferably 0.5 mg to 250 mg per day and more preferably 1 mg to 50 mg. Daily doses of DHA and carotenoids are preferably 50 mg to 3,000 mg and 0.5 mg to 250 mg, respectively and more preferably 100 mg to 2,200 mg and 1 mg to 50 mg, respectively. A ratio between the DHA content and the carotenoid content (as a total amount) is preferably 100:1 to 1:50 and more preferably 50:1 to 10:1.

For example, when the brain function-improving composition of the present invention includes DHA and capsanthin, or DHA, capsanthin, lutein, and zeaxanthin as active ingredients, preferred daily doses of DHA and carotenoids are 100 mg to 1,500 mg and 1 mg to 100 mg, respectively because dementia in humans can be prevented, and their more preferred doses are 300 mg to 1,200 mg and 1 mg to 20 mg, respectively.

When the inhibitory agent of amyloid $\beta$ accumulation in the hippocampus of the present invention includes DHA as an active ingredient, a daily dose of DHA is preferably 50 mg to 3,000 mg and more preferably 100 mg to 2,200 mg. When the inhibitory agent of amyloid $\beta$ accumulation in the hippocampus of the present invention includes one or more kinds of carotenoids as active ingredients, a daily dose of each carotenoid is preferably 0.5 mg to 250 mg and more preferably 1 mg to 50 mg. When the inhibitory agent of amyloid $\beta$ accumulation in the hippocampus of the present invention includes a combination of DHA and carotenoids as active ingredients, a ratio between the DHA content and the carotenoid content (as a total amount) is preferably 100:1 to 1:50 and more preferably 50:1 to 10:1.

The content and dosage of DHA may be represented as a conversion amount expressed in terms of a fatty acid composition ratio of DHA. The definition of a conversion amount expressed in terms of a fatty acid composition ratio is explained in Examples below.

When the composition of the present invention includes two or more kinds of carotenoids, there are no particular limitations on a content ratio of the two or more kinds of carotenoids. For example, when two or more kinds of carotenoids are fucoxanthin, fucoxanthinol, capsorbin, and capsanthin, it is preferable that the content ratio thereof is arranged in such a manner that when a particular carotenoid is given as a ratio of 1, other carotenoids are within a ratio of 100 (a particular carotenoid : each of other carotenoids=1: more than 0 and up to 100). It is more preferable that a content ratio is arranged in such a manner that when a particular carotenoid is given as a ratio of 1, other carotenoids are within a ratio of 10 (a particular carotenoid: each of other carotenoids=1:more than 0 and up to 100).

It is noted that the dosages described above are merely an example, and when a formulation is improved in bioabsorbability and bioavailability by a formulation technique and can thus exert its effect at a lower concentration, the above dosages can be reduced to a lower concentration for application.

As long as the composition of the present invention includes the ingredients mentioned above as active ingredients, it may further include an ingredient other than the above and a pharmacologically acceptable base. As one example of a pharmacologically acceptable base, there is an ingredient ensuring stability mainly during storage and distribution (for example, a storage stabilizer). In addition, one or more ingredients (preferably about one to three kinds and more preferably about one kind) selected from various ingredients constituting a desired final product (e.g., a food or drink product, a pharmaceutical product, and a quasi-pharmaceutical product) may also be included.

The agent or the composition of the present invention can be used as a final product as it is. Alternatively, it can be used as an additive for a food or drink product, an additive for a pharmaceutical product, or an additive for a quasi-pharmaceutical product. In this way, various effects can be imparted to the food or drink product, the pharmaceutical product, and the quasi-pharmaceutical product.

A pharmacologically acceptable base is not particularly limited so long as the objects of the present invention are not impaired. For example, one or more kinds of bases can be selected from excipients, disintegrating agents, binding agents, lubricant, coating agents, coloring agents, color formers, taste masking agents, flavoring agents, antioxidants, antiseptics, tasting agents, acidulants, sweeteners, fortifiers, vitamin compounds, inflating agents, thickeners, surfactants, and the like, as far as they do not impair various properties essential for formulation (e.g., formulation stability) and are suited to a preparation form of a final product (e.g., a pharmaceutical product, a quasi-pharmaceutical product, and a food or drink product). Further, a pharmacologically acceptable base may be other ingredient having an inhibitory effect on nitrogen monoxide production.

When the agent or the composition of the present invention includes a pharmacologically acceptable base, a compounding amount of an active ingredient (a total amount thereof if two or more ingredients are used in combination) is not particularly limited so long as the effective amount is attained, however it is usually within a range of 0.01 to 80 mass %.

A form of administration of the agent or the composition of the present invention is usually oral administration such as buccal administration and sublingual administration.

A preparation form of the agent or the composition of the present invention can be suitably determined depending on whether the agent or the composition is made into a food or drink product, a pharmaceutical product, or a quasi-pharmaceutical product, and is not particularly limited. Examples of the preparation form for oral administration may include liquid forms (liquid agents), syrup forms (syrup agents), tablets, capsule forms (capsules), powder forms (granule forms (granules), fine particles (powders)), soft capsule forms (soft capsules), solid forms (solid preparation), semi-liquid forms, cream forms, and paste forms.

When the composition of the present invention is used as a brain-function improving composition (a composition for inhibiting deterioration of brain functions and a composition for improving memory and learning), subjects of administration may be patients with a cognitive disease such as dementia, but are not necessarily diagnosed with dementia. Subjects may also include the ones, who have a risk of suffering from dementia, who don't want to suffer from dementia, or who the third party wants not to suffer from dementia. Further, subjects may be patients with mild cognitive impairment, but are not necessarily diagnosed with mild cognitive impairment, and subject may include the ones, who have a risk of developing mild cognitive impairment, who don't want to suffer from mild cognitive impairment, or who the third party wants not to suffer from mild cognitive impairment. Examples of such subjects may include the ones, who feel that their brain functions (e.g., memory and activities of daily living) have been deteriorated, who have an Alzheimer's disease patient or a patient with mild cognitive impairment in their relatives, who are elderly persons, and who want to improve memory and learning abilities. Even subjects who have no particular concern can routinely take it for the purposes of preventing dementia, mild cognitive impairment, and deterioration of brain functions, improving brain functions, and the like.

Dementia is as defined in ICD-10 (International Statistical Classification of Diseases and Related Health Problems, 10th Revision.) and DSM-IV (Diagnostic and Statistical Manual of Mental Disorders, Fourth Edition, edited by American Psychiatric Association.). In essence, dementia refers to a condition where intellectual functions that have been once normally developed are continuously deteriorated due to an acquired organic disorder, thereby causing inconvenience in daily life and/or social activity without having impaired consciousness. Diagnostic criteria for dementia is usually judged by finding the following symptoms (1) to (6) (Textbook for Dementia/edited by Japan Society for Dementia Research, published by Chugai-Igakusha):

(1) A core symptom of dementia is accompanied by deficits in intellectual functions, represented by memory impairment, and multiple deficits in intellectual functions, such as aphasia, apraxia, agnosia and executive function disorder are observed;
(2) Since these deficits in intellectual functions are an acquired illness, there is an observation in a symptom that once developed intelligence is deteriorated;
(3) There is an organic change of the brain, thus a symptom is based on physical abnormalities in the brain;
(4) Deficits need to persist for a certain time period. According to ICD-10, they should be present for "a minimum duration of six months";
(5) Deficits in intellectual functions result in a symptom having significant impairment in social or daily life activity;
(6) The above symptoms are not acute or temporary, but observed without having impaired consciousness.

Mild cognitive impairment (MCI) is a precondition for dementia, a condition in which cognitive functions are deteriorated more than what would be expected on the basis of normal physiological process of aging.

The composition for inhibiting amyloid $\beta$ accumulation in the brain of the present invention can prevent the onset of the Alzheimer's disease by preventing various disturbances of nerve cells caused by amyloid $\beta$ in the brain. Amyloid $\beta$ is always synthesized even in a healthy person, however amyloid $\beta$ is always removed by a degrading enzyme such as neprilysin, and the like in a healthy person to avoid accumulation of amyloid $\beta$. It is considered that the Alzheimer's disease is triggered by accumulation of amyloid $\beta$ by losing a balance between its synthesis and degradation. Since the composition for inhibiting amyloid $\beta$ accumulation in the brain of the present invention can inhibit amyloid $\beta$ accumulation, it can suppress the onset of the Alzheimer's disease. Further, the Alzheimer's disease has such characteristics that amyloid $\beta$ is accumulated in the brain in a stage before deterioration of functions are confirmed by brain function evaluations (i.e., a normal condition in terms of cognitive functions, thus not being diagnosed with the Alzheimer's disease). In this aspect, the composition of the present invention can prevent MCI, a preclinical stage of Alzheimer's disease, not yet being diagnosed with the Alzheimer's disease as well as deterioration of brain functions occurring in a normal range of a healthy person.

Consequently, the composition for inhibiting amyloid $\beta$ accumulation in the brain of the present invention can be used as a food or drink product or a pharmaceutical product for a purpose of preventing deterioration of brain functions for those, as mentioned above, with the Alzheimer's disease or in a preclinical stage thereof, namely MCI, as well as for completely healthy persons. Subjects of administration of the composition for inhibiting amyloid $\beta$ accumulation in the brain are not particularly limited, but the composition is suitable, for example, for patients with a various forms of dementia including the Alzheimer's disease and with mild cognitive impairment, as well as healthy persons who have the feeling of being forgetful in a daily life and the feeling of being discomfort due to poor concentration and the like. Even subjects who have no particular concern can routinely take it for the purpose of preventing the Alzheimer's disease. Further accumulation of amyloid $\beta$ is also involved in various age-related diseases that include ocular diseases such as age-related macular degeneration and glaucoma caused by accumulation of amyloid $\beta$ in the retina, and vascular disorders caused by accumulation of amyloid $\beta$ in vascular walls. Thus the composition of the present invention can be administered for a purpose of preventing these diseases.

There are no particular limitations on the timing of administration of the agent or the composition of the present invention.

Further, the agent or the composition of the present invention may be used as a healthy food, a functional food, a nutritional supplement (supplement), a food for specified health use, a food for medical use, a food for the sick, an infant food, a food for nursing care, a food for the elderly, and the like.

EXAMPLES

Examples 1 and 2 and Comparative Examples 1 to 3

[A Passive Avoidance Test (1) after Three-Month Feeding]

Six-week old SAMP8 (Japan SLC Inc.) were fed with the powder feed CE-2 (Japan SLC Inc.) containing a test sample listed in Table 1. Ingredients used for each test sample were as following:

TG-DHA: DD oil DHA-46; Nippon Suisan Kaisha, Ltd. (DHA of this product is contained primarily as a DHA in triglyceride form. Assuming that fatty acids contained in a raw material are all free fatty acids, a composition ratio of the corresponding fatty acid to total fatty acids is defined as a "fatty acid composition ratio" of the corresponding fatty acid. In this product, a fatty acid composition ratio of DHA was 46%.)

Capsanthin: A composition containing 20% capsanthin derived from paprika: Katra Phytochem Private Ltd.

Lutein+zeaxanthin: Lutein derived from marigold/zeaxanthin mixture: 10%: 10% mixture: Katra Phytochem Private Ltd.

A compounding amount of docosahexaenoic acid was 1,333 mg/kg/day (617 mg/kg/day in a conversion amount expressed in terms of a fatty acid composition ratio). A compounding amount of each ingredient other than docosahexaenoic acid was 100 mg/kg/day (20 mg/kg/day in terms of the carotenoid content). Drinking water could be freely accessed. Food was exchanged once three days and continued to supply for 3 months. Subsequently, a step through passive avoidance test was performed. This test is one of testing methods for memory learning ability that utilizes the habit of mice liking a dark place. The method involves the following steps: when a mouse moves from a lighted compartment to a dark compartment, electric stimulation is delivered for memory retention, and 24 hours after stimulation, "to what extent the mouse remembers that the dark compartment is dangerous" is evaluated by the length of a time of the staying in the lighted compartment. That is, the length of a time of the staying in the lighted compartment represents the level of memory learning ability. Analysis was performed by using software called ShutAvoid (Panlab S.L.U). For preliminary learning on the first day, the time until a mouse entered the dark compartment (latency) was set to 2 minutes at maximum. After the mouse was placed in the lighted compartment and habituated for 1 minute, a shielding door was opened. When the mouse entered the dark compartment, the door was closed and electric stimulation was delivered at 0.4 mA for 2 seconds. Once the electric stimulation was delivered, the mouse was immediately returned to a home cage. For a main test on the second day, the latency was set to 5 minutes at maximum and the staying time in the lighted compartment was measured. The latency of individuals, which continued to stay in the lighted compartment for 5 minutes on the second day, was calculated as 5 minutes.

A conversion amount expressed in terms of a fatty acid composition ratio of a fatty acid of interest is a value calculated by multiplying the fatty acid content in a row material by a fatty acid composition ratio of the corresponding fatty acid.

The staying time in the lighted compartment on the second day was averaged for each group to calculate a ratio to a control group (non-intake group) being set as 1.0. The number of individuals in each group was as following: 28 in a control group (Comparative Example 1), 23 in a TG-DHA group (Comparative Example 2), 7 in a TG-DHA+capsanthin group (Example 1), 8 in a capsanthin group (Comparative Example 3), and 8 in a TG-DHA+lutein+zeaxanthin+capsanthin group (Example 2). Each result of Comparative Examples 1 to 3 and Examples 1 and 2 were shown in Table 1.

TABLE 1

PASSIVE AVOIDANCE TEST

| | TEST SAMPLE | NUMBER OF INDIVIDUALS | PASSIVE AVOIDANCE TEST FOR SAMP8 (RATIO RELATIVE TO CONTROL) |
|---|---|---|---|
| COMPARATIVE EXAMPLE 1 | CONTROL (NORMAL DIET) | 28 | 1.0 |
| COMPARATIVE EXAMPLE 2 | TG-DHA | 23 | 1.0 |
| COMPARATIVE EXAMPLE 3 | CAPSANTHIN | 8 | 0.8 |
| EXAMPLE 1 | TG-DHA + CAPSANTHIN | 7 | 1.1 |
| EXAMPLE 2 | TG-DHA + LUTEIN + ZEAXANTHIN + CAPSANTHIN | 8 | 1.4 |

As is evident from Table 1, samples in Examples 1 and 2 showed a higher passive avoidance learning effect than those in Comparative examples 1 to 3. Especially it was revealed that a combination of TG-DHA +lutein +zeaxanthin+ capsanthin (Example 2) showed 1.4 folds more effective than a control in the passive avoidance learning. Further, a combination of TG-DHA+lutein+zeaxanthin (Example 2) had the passive avoidance learning effect of 1:1 relative to a control. This result indicates that the internal composition of the present invention has a brain-function improving effect.

Examples 3 to 5 and Comparative Examples 4 to 6

[A Passive Avoidance Test after Six-Month Feeding]

A test was performed in the same manner as in the passive avoidance test (1) after three-month feeding except that a test sample shown in Table 2 was used and a term of feeding was changed to 6 months. The results are shown in Table 2.

TABLE 2

PASSIVE AVOIDANCE TEST

| | TEST SAMPLE | NUMBER OF INDIVIDUALS | PASSIVE AVOIDANCE TEST FOR SAMP8 (RATIO RELATIVE TO CONTROL) |
|---|---|---|---|
| COMPARATIVE EXAMPLE 4 | CONTROL (NORMAL DIET) | 34 | 1.00 |

TABLE 2-continued

PASSIVE AVOIDANCE TEST

| | TEST SAMPLE | NUMBER OF INDIVIDUALS | PASSIVE AVOIDANCE TEST FOR SAMP8 (RATIO RELATIVE TO CONTROL) |
|---|---|---|---|
| COMPARATIVE EXAMPLE 5 | TG-DHA | 19 | 0.84 |
| COMPARATIVE EXAMPLE 6 | CAPSANTHIN | 9 | 0.93 |
| EXAMPLE 3 | TG-DHA + CAPSANTHIN | 10 | 0.86 |
| EXAMPLE 4 | TG-DHA + LUTEIN + ZEAXANTHIN | 8 | 1.07 |
| EXAMPLE 5 | TG-DHA + LUTEIN + ZEAXANTHIN + CAPSANTHIN | 19 | 1.55 |

As is evident from Table 2, a combination of TG-DHA+lutein+zeaxanthin (Example 4) and a combination of TG-DHA+lutein+zeaxanthin+capsanthin (Example 5) showed the passive avoidance learning effect, and of those, the latter combination had a remarkable effect. These results indicate that the internal composition of the present invention has a brain-function improving effect, especially a combination of TG-DHA+lutein+zeaxanthin+capsanthin (Example 5) exhibits a more remarkable brain-function improving effect when administered for a long period of time.

[Measurement of Inhibitory Activity of Amyloid β Accumulation in Brain]

From each mouse used in Comparative Example 4 and Example 5 in the previous section, a part of hippocampus was extracted and the amount of amyloid β protein therein was quantitatively determined. The extracted brain was added with 70% formate and homogenized. Subsequently, ultracentrifugation (100,000 G×20 min) was performed to separate a supernatant. A part of the supernatant was used to determine the quantity of amyloid β according to a protocol of a Human/Rat β Amyloid 42 ELISA Kit (Wako Pure Chemical Industries, Ltd.). Results of ELISA are shown in Table 3.

TABLE 3

AMYLOID β AMOUNT IN HIPPOCAMPUS

| | | NUMBER OF INDIVIDUALS | AMOUNT OF Aβ 42 (pg/mg HIPPOCAMPUS WEIGHT) |
|---|---|---|---|
| COMPARATIVE EXAMPLE 4 | CONTROL (NORMAL DIET) | 4 | 1.74 ± 0.15 |
| EXAMPLE 5 | TG-DHA + LUTEIN + ZEAXANTHIN + CAPSANTHIN | 3 | 1.20 ± 0.019 |

From results shown in Table 3, it was found that, in a TG-DHA+lutein+zeaxanthin+capsanthin group (Example 5), an inhibitory effect of amyloid β accumulation was enhanced and amyloid β 42 was significantly reduced.

Further, in a group in which a combination of TG-DHA+lutein+zeaxanthin was administered (Example 4), the amount of the amyloid β 42 was 1.59±0.23 pg/mg hippocampus weight. Taking the results in Tables 1 to 3 into consideration, it is speculated that the test samples in Examples 1 to 4 also promote a reduction of amyloid β 42 in the same manner as those in Examples 4 and 5.

A western blotting of the rest of the supernatant was performed to measure a polymerization degree according to a molecular weight pattern. As a result, it was found that, in samples from a group in which TG-DHA+lutein+zeaxanthin+capsanthin was administered (Example 5), a fraction of amyloid β having a high polymerization degree was reduced. From this result, it was considered that the amount of amyloid p accumulated in the brain was reduced and amyloid β was polymerized to a lesser extent by administrating TG-DHA+lutein+zeaxanthin+capsanthin. Since amyloid β is known to exhibit strong neurotoxicity by polymerizing several or more molecules thereof, it was considered that TG-DHA+lutein+zeaxanthin+capsanthin had an effect of prophylactically protecting a nerve cell in the brain from being damaged when orally administrated. This result indicates that the internal composition of the present invention can inhibit amyloid β accumulation in the hippocampus.

Examples 6 and 7 and Comparative Examples 7 to 9

[A Passive Avoidance Test (2) After Three-Month Feeding]

A test was performed in the same manner as the passive avoidance test (1) after three-month feeding, except that seven-week old male SAMP8 mice (Japan SLC Inc.) were used, a test sample shown in Table 4 was used, the number of individuals were set to 10 to 12 in each Example, and DHA used in Example 6 and Comparative Example 9 was a DHA in phosphatidylcholine form (PC-DHA: DHA content of 18.0% or more, phospholipid content of 25.0% or more: SUNOMEGA (registered trademark) PC-DHA, manufactured by NOF Corp.). The results are shown in Table 4.

TABLE 4

PASSIVE AVOIDANCE TEST

| | TEST SAMPLE | NUMBER OF INDIVIDUALS | DOSAGE OF DHA (CONVERSION VALUE EXPRESSED IN TERMS OF FATTY ACID COMPOSITION RATIO) (mg/kg/day) | PASSIVE AVOIDANCE TEST FOR SAMP8 (RATIO RELATIVE TO CONTROL) |
|---|---|---|---|---|
| COMPARATIVE EXAMPLE 7 | CONTROL | 11 | — | 1.0 |
| COMPARATIVE EXAMPLE 8 | TG-DHA | 10 | 617 | 1.6 |
| EXAMPLE 6 | TG-DHA + LUTEIN + ZEAXANTHIN + CAPSANTHIN | 11 | 617 | 2.7 |
| COMPARATIVE EXAMPLE 9 | PC-DHA | 12 | 240 | 1.6 |
| EXAMPLE 7 | PC-DHA + LUTEIN + ZEAXANTHIN + CAPSANTHIN | 12 | 240 | 2.4 |

As is evident from Table 4, a remarkable passive avoidance learning effect was observed in Examples 6 and 7, as compared with Comparative Examples 7 to 9. Although high absorbability and transportability to the brain of PC-DHA have been known, these results indicate that the internal composition of the present invention can obtain a remarkable brain-function improving effect when any of a DHA in phospholipid form and a DHA in triglyceride form is used as DHA. Furthermore, it was revealed that PC-DHA exhibited a similar effectiveness even with a lower concentration of DHA.

Formulation Examples

An ingredient shown in Table 5 below was suspended in a medium chain fatty acid triglyceride and a soft capsule was prepared by using a gelatin by a routine procedure.

TABLE 5

FORMULATION EXAMPLE (BRAIN-FUNCTION IMPROVING COMPOSITION)

| | FORMULATION EXAMPLE 1 | FORMULATION EXAMPLE 2 | FORMULATION EXAMPLE 3 |
|---|---|---|---|
| DHA | 80 mg | 80 mg | 80 mg |
| LUTEIN | | 2 mg | 2 mg |
| ZEAXANTHIN | | | 2 mg |
| CAPSANTHIN | 2 mg | 2 mg | 2 mg |
| | TOTAL 82 mg/CAPSULE | TOTAL 84 mg/CAPSULE | TOTAL 86 mg/CAPSULE |

It is noted that the amount of each ingredient in Table 5 is expressed as a conversion amount in terms of a fatty acid composition ratio or as a carotenoid content.

The invention claimed is:

1. An internal composition comprising: docosahexaenoic acid and capsanthin; or docosahexaenoic acid, capsanthin, lutein, and zeaxanthin.

2. The internal composition according to claim 1, wherein the internal composition is a brain-function improving composition.

3. The internal composition according to claim 1, wherein the internal composition is a composition for inhibiting amyloid β accumulation in the brain.

4. The internal composition according to claim 1, wherein an active ingredient is docosahexaenoic acid, capsanthin, lutein, and zeaxanthin.

* * * * *